United States Patent
Liu et al.

(10) Patent No.: US 8,755,486 B2
(45) Date of Patent: Jun. 17, 2014

(54) METHOD FOR PLACING A/D CONVERTER, FRONT-LIT DETECTOR AND CT APPARATUS

(75) Inventors: Zhiqiang Liu, Beijing (CN); Qinglei Li, Beijing (CN); Yu Zhou, Beijing (CN)

(73) Assignee: GE Medical Systems Global Technology, LLC, Waukesha, WI (US)

( * ) Notice: Subject to any disclaimer, the term of this patent is extended or adjusted under 35 U.S.C. 154(b) by 353 days.

(21) Appl. No.: 13/271,077

(22) Filed: Oct. 11, 2011

(65) Prior Publication Data
US 2012/0093283 A1  Apr. 19, 2012

(30) Foreign Application Priority Data
Oct. 15, 2010 (CN) .......................... 2010 1 0522068

(51) Int. Cl.
*H05G 1/24* (2006.01)
*H01J 31/49* (2006.01)
*H01L 27/146* (2006.01)
*G01T 1/24* (2006.01)
*G01T 1/20* (2006.01)

(52) U.S. Cl.
USPC ....... 378/19; 378/98.8; 378/189; 250/370.09; 250/370.14

(58) Field of Classification Search
CPC ......... H05G 1/24; H01J 31/49; H01L 27/146; G01T 1/24; G01T 1/20
USPC .............. 378/19, 91, 98, 98.8, 189, 204, 210; 250/336.1, 358.1, 361 R, 362, 363.01, 250/363.02, 363.08, 370.01, 370.08, 250/370.09, 370.11, 370.14, 371, 393, 395, 250/526
See application file for complete search history.

(56) References Cited

U.S. PATENT DOCUMENTS

| 6,931,092 B2 * | 8/2005 | Joshi et al. ...................... 378/19 |
| 6,990,176 B2 * | 1/2006 | Sherman et al. ............. 378/98.8 |
| 7,065,173 B2 * | 6/2006 | Lacey et al. ..................... 378/19 |
| 7,379,528 B2 * | 5/2008 | Mattson et al. ................. 378/19 |
| 7,439,516 B2 | 10/2008 | Zeman et al. |
| 2003/0227998 A1 | 12/2003 | Liao |
| 2010/0091128 A1 | 4/2010 | Ogasawara et al. |

* cited by examiner

*Primary Examiner* — Anastasia Midkiff
(74) *Attorney, Agent, or Firm* — Armstrong Teasdale LLP

(57) ABSTRACT

A front-lit detector includes a collimator, an X-ray to visible light converter configured to convert X-rays to visible light after the X-rays pass through the collimator to irradiate the X-ray to visible light converter, a visible light to analog signal converter configured to cover the visible light into analog signals, a substrate on which the visible light to analog signal converter is placed, and an A/D converter configured to convert the analog signals into digital signals.

17 Claims, 2 Drawing Sheets

US 8,755,486 B2

METHOD FOR PLACING A/D CONVERTER, FRONT-LIT DETECTOR AND CT APPARATUS

CROSS REFERENCE TO RELATED APPLICATIONS

This application claims the benefit of Chinese Patent Application No. 201010522068.8 filed Oct. 15, 2010, which is hereby incorporated by reference in its entirety.

BACKGROUND OF THE INVENTION

The embodiments described herein generally relate to the technical field of CT imaging, in particular to a method for placing A/D converter, a front-lit Detector and a CT apparatus.

Detector is one of the most important components in a CT apparatus. The detector is used for converting X-rays emitted from a tube into electrical signals. Then an A/D converter converts the analog electrical signals into digital signals. Since the A/D converter is too large in size to be packaged in the detector, it is necessary to lead the analog electrical signals out of the detector, so that the A/D converter outside the detector converts the analog electrical signals into digital signals for further processing.

As we know, a detector will usually output hundreds and even thousands of analog electrical signals, so outputting the analog electrical signals out of the detector not only requires gigantic cables but also have critical requirements for signal integrity.

With the development of the ASIC (Application Specific Integrated Circuit) design technology, the size of the A/D converter has become small and the power thereof low enough to allow the A/D converter to be placed in the detector.

However, it is well-known that X-rays will damage the ASIC chips, thus how to place the A/D converter in the detector without being irradiated by the X-rays is the research hotspot at present.

U.S. Pat. No. 7,439,516, titled "Module assembly for multiple die back-illuminated diode" provides a solution of back-illuminated detector, which places the A/D converter between the diode and the substrate and is mainly used for high-end CT apparatus. Such a technical solution costs much and changes the structure of the back-illuminated detector a lot.

BRIEF DESCRIPTION OF THE INVENTION

The embodiments described herein provide a method of placing the A/D converter in the front-lit detector with least structure modification made to the detector as well as a front-lit detector and a CT apparatus.

In one aspect, a front-lit detector includes a collimator, an X-ray to visible light converter, a visible light to analog signal converter, a substrate, and an A/D converter converting the analog signals into digital signals. The X-rays irradiate on the X-ray to visible light converter after passing through the collimator, and are converted into visible light by the X-ray to visible light converter. The visible light to analog signal converter, which is placed on the substrate, converts the visible light into analog signals.

Preferably, the A/D converter is provided above or under the elongated plate of the substrate.

Preferably, the A/D converter is provided under the substrate and a shielding piece is provided between the substrate and the visible light to analog signal converter.

Preferably, the A/D converter is provided under the substrate and a shielding piece is embedded into the upper end of the substrate.

In addition, the front-lit detector of the present invention further comprises a heat sink provided on the side of the A/D converter that is away from the substrate.

The shielding piece uses a high density material.

The thermal expansion coefficient of the shielding piece is close to that of the visible light to analog signal converter.

In another aspect, a method of placing the A/D converter in the front-lit detector is provided. The front-lit detector includes a collimator, an X-ray to visible light converter, a visible light to analog signal converter and a substrate. The X-rays irradiate on the X-ray to visible light converter after passing through the collimator, and are converted into visible light by the X-ray to visible light converter. The visible light to analog signal converter, which is placed on the substrate, converts the visible light into analog signals. The method includes providing the A/D converter at a position on the substrate that is not irradiated by the X-rays.

Preferably, providing the A/D converter at a position on the substrate that is not irradiated by the X-rays further includes elongating the substrate, and providing the A/D converter above or under the elongated plate of the substrate.

Preferably, providing the A/D converter at a position on the substrate that is not irradiated by the X-rays further includes providing the A/D converter under the substrate, and providing a shielding piece between the substrate and the visible light to analog signal converter.

Preferably, providing the A/D converter at a position on the substrate that is not irradiated by the X-rays further includes providing the A/D converter under the substrate, and embedding a shielding piece into the upper end of the substrate.

In addition, the method of placing the A/D converter into the front-lit detector further includes providing a heat sink on the side of the A/D converter that is away from the substrate.

The shielding piece uses a high density material.

The thermal expansion coefficient of the shielding piece is close to that of the visible light to analog signal converter.

In yet another aspect, a CT apparatus having a front-lit detector is provided. The front-lit detector includes a collimator, an X-ray to visible light converter, a visible light to analog signal converter, a substrate, and an A/D converter converting the analog signals into digital signals. The X-rays irradiate on the X-ray to visible light converter after passing through the collimator, and are converted into visible light by the X-ray to visible light converter. The visible light to analog signal converter, which is placed on the substrate, converts the visible light into analog signals.

Preferably, the A/D converter is provided above or under the elongated plate of the substrate.

Preferably, the A/D converter is provided under the substrate and a shielding piece is provided between the substrate and the visible light to analog signal converter.

Preferably, the A/D converter is provided under the substrate and a shielding piece is embedded into the upper end of the substrate.

In addition, the CT apparatus further includes a heat sink provided on the side of the A/D converter that is away from the substrate.

The shielding piece uses a high density material.

Compared to the prior art, the method of placing the A/D converter into the front-lit detector as well as the front-lit detector and CT apparatus described herein have the following advantageous effects.

The embodiments described herein place the A/D converter into the detector with least structure modification made to the detector, meanwhile, the A/D converter is protected from being irradiated by X-rays.

In addition, the embodiments described herein modularize the structure of the detector, increases the flexibility and reliability of the design of the detector, make maintenance of the detector easier, and reduce the maintenance cost of the detector.

BRIEF DESCRIPTION OF THE DRAWINGS

In order to make a more thorough understanding of the disclosure, reference is made to the following descriptions taken with reference to the figures.

DETAILED DESCRIPTION OF THE INVENTION

The specific embodiments of the present invention will be described in detail below, but the present invention is not limited to the specific embodiments.

Figure 1:
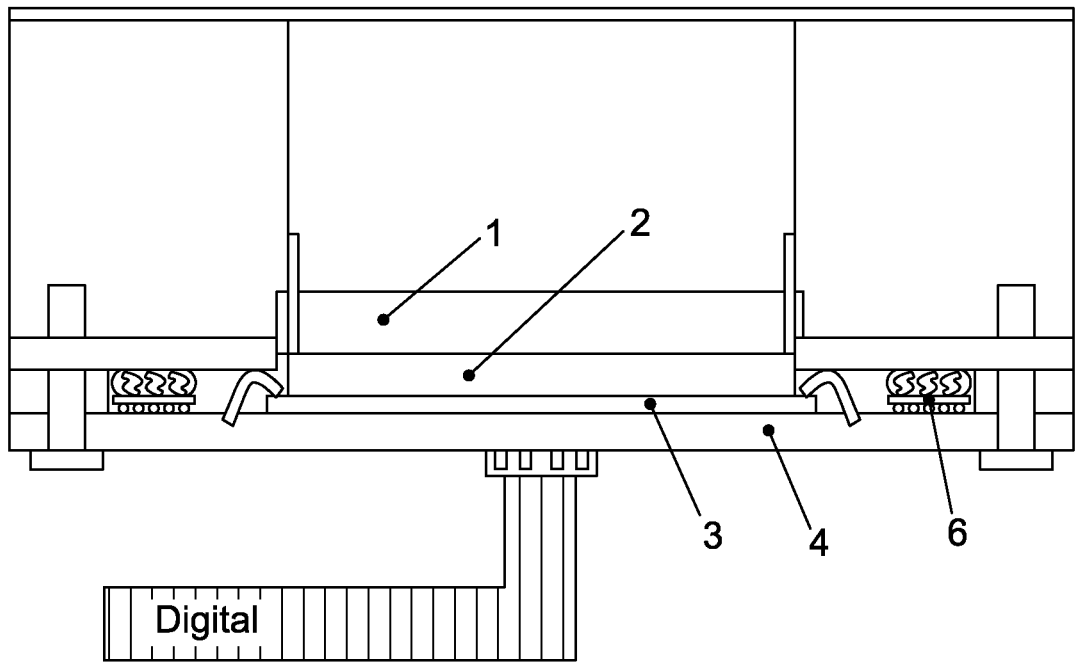
FIG. 1 is a schematic diagram of an exemplary embodiment of the front-lit detector.
Figure 2:
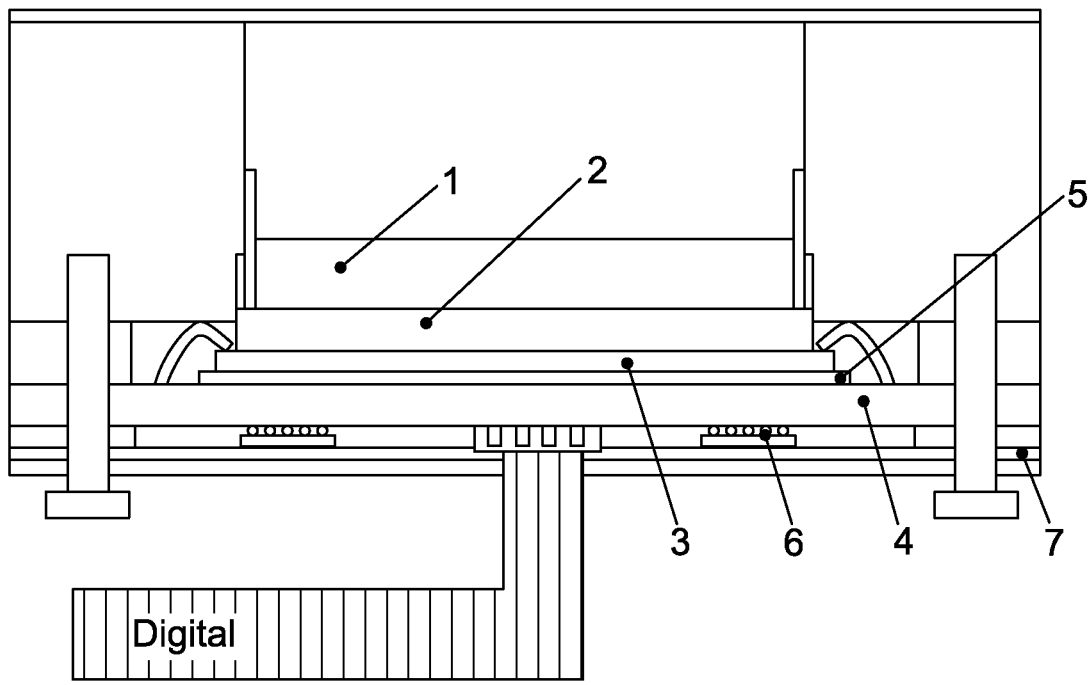
FIG. 2 is a schematic diagram of a first alternative embodiment of the front-lit detector.
Figure 3:
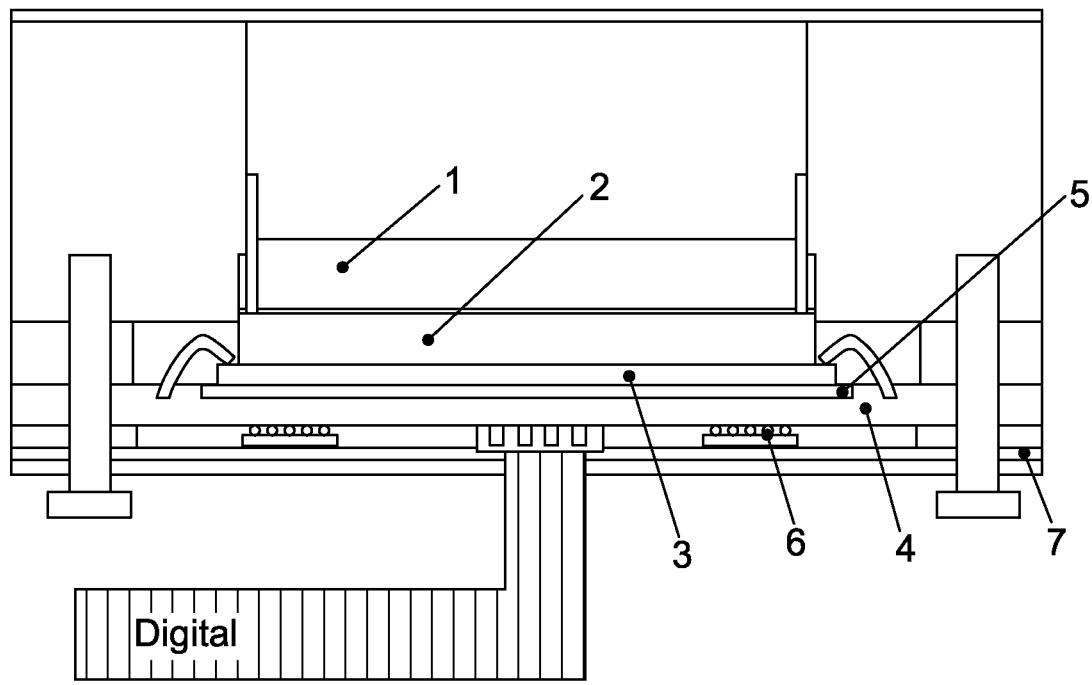
FIG. 3 is a schematic diagram of a second alternative embodiment of the front-lit detector.

As shown in FIGS. 1-3, the front-lit detector includes a collimator 1, an X-ray to visible light converter 2, a visible light to analog signal converter 3 and a substrate 4. The X-rays irradiate on the X-ray to visible light converter 2 after passing through the collimator 1, and are converted into visible light by the X-ray to visible light converter 2. The visible light to analog signal converter 3, which is placed on the substrate 4, converts the visible light into analog signals. The analog signals are connected to the substrate 4 through wire bonding. Moreover, the front-lit detector further includes an A/D converter 6 converting the analog signals into digital signals.

Wherein, the collimator 1 is used to filter stray X-rays and reduce interference of the X-rays between adjacent pixels. The X-ray to visible light converter 2 usually uses a Scintillator pack (which is sintered by a special material). The visible light to analog signal converter 3 may be a diode. The substrate 4 may be a multi-layered circuit board using fibre glass or ceramics as the insulating material.

In one embodiment of the front-lit detector shown in FIG. 1, it can be seen that the A/D converter 6 is provided above or under the elongated plate of the substrate 4. The A/D converter 6 is not positioned within the X-ray beam, thus it is not subjected to any X-ray damage.

In another embodiment of the front-lit detector shown in FIG. 2, the A/D converter 6 is provided under the substrate 4 and a shielding piece 5 is provided between the substrate 4 and the visible light to analog signal converter 3. The shielding piece 5 should be long enough to cover the A/D converter 6.

In yet another embodiment of the front-lit detector shown in FIG. 3, the A/D converter 6 is provided under the substrate 4 and a shielding piece 5 is embedded into the upper end of the substrate 4.

The shielding piece 5 uses a high density material, such as a tungsten slice. In this way, although the A/D converter 3 is still in the range of X-ray irradiation, the shielding piece 5 such as a tungsten slice will block the X-rays from irradiating on the A/D converter 3, thus the A/D converter 3 will not be irradiated by the X-rays and will not be damaged by irradiation of the X-rays.

In addition, the thermal expansion coefficient of the shielding piece 5 is preferably close to the thermal expansion coefficient of the visible light to analog signal converter 3, thus avoiding deformation of the visible light to analog signal converter due to the different thermal expansion coefficient.

Referring again to FIGS. 1-3, the front-lit detector further includes a heat sink 7 provided on the side of the A/D converter that is away from the substrate 4. The heat sink 7 can carry away heat produced by the A/D converter 6 more quickly so as to reduce the influence to the visible light to analog signal converter by the change in temperature.

Although the heat sink 7 is used herein to dissipate the heat of the A/D converter 6, any method for dissipating heat known to those skilled in the art can be used.

The A/D converter 6 can be an A/D converter with low current and having a multi-channel switching function, for example, the vyper series developed by GE, the ADAS series of AD Corporation, etc. The substrate 4 can be selected as a multi-layered circuit board made of ceramics or fibre glass depending on the requirements on the number of layers and smoothness. The A/D with a corresponding number of channels is soldered on the substrate 4 by means of reflow soldering, taking chips of the vyper series as an example, 8 A/D chips need to be soldered on the substrate of a detector of 32 rows.

With respect to FIG. 3, since the shielding piece 5 is embedded into the upper end of the substrate 4 so as to connect the substrate 4 to the visible light to analog signal converter 3 through the shielding piece 5, the substrate 4 herein can be called a hybrid circuit board.

In another aspect a method of placing the A/D converter in a front-lit detector is provided. The front-lit detector includes a collimator 1, an X-ray to visible light converter 2, a visible light to analog signal converter 3 and a substrate 4. The X-rays irradiate on the X-ray to visible light converter 2 after passing through the collimator 1, and are converted into visible light by the X-ray to visible light converter 2. The visible light to analog signal converter 3, which is placed on the substrate 4, converts the visible light into analog signals.

The method includes providing the A/D converter 6 on a position of the substrate 4 that cannot be irradiated by X-rays.

Three methods of carrying out the above-mentioned step will be introduced below. It shall be noted that although only three methods are introduced herein, the present invention is not limited to said three methods, and any method known to those skilled in the art can be used.

One embodiment of the method includes elongating the substrate 4, and providing the A/D converter above or under the elongated plate of the substrate.

We know that if the substrate 4 is elongated, the elongated plate cannot be irradiated by X-rays, thus providing the A/D detector 6 on the elongated plate of the substrate can avoid the possibility of damage to the A/D detector 6 owing to X-ray irradiation.

Another embodiment of the method includes providing the A/D converter 4 under the substrate 4, and providing a shielding piece 5 between the substrate 4 and the visible light to analog signal converter 3.

This embodiment of the method does not elongate the substrate 4, but a shielding piece 5 is provided between the substrate 4 and the visible light to analog signal converter 3 in order to prevent the A/D converter 4 from being irradiated by X-rays. Since the shielding piece 5 can block X-rays, it can effectively protect the A/D converter 4.

Yet another embodiment of the method includes providing the A/D converter 4 under the substrate 4, and embedding a shielding piece 5 into the upper end of the substrate 4.

This embodiment of the method has the shielding piece 5 embedded into the upper end of the substrate 4, i.e. the surface where the substrate 4 contacts the visible light to analog signal converter 3, thus achieving the same effect as the previous method.

Furthermore, in order to dissipate heat produced by operation of the A/D converter, the method of placing the A/D converter in the front-lit detector further includes providing a heat sink 7 on the side of the A/D converter 6 that is away from the substrate 4.

For the shielding piece 5, it uses a high density material, and the thermal expansion coefficient thereof is preferably close to that of the visible light to analog signal converter 3.

In yet another aspect CT apparatus having a front-lit detector is provided. The front-lit detector includes a collimator 1, an X-ray to visible light converter 2, a visible light to analog signal converter 3 and a substrate 4. The X-rays irradiate on the X-ray to visible light converter 2 after passing through the collimator 1, and are converted into visible light by the X-ray to visible light converter 2. The visible light to analog signal converter 3, which is placed on the substrate 4, converts the visible light into analog signals. The front-lit detector further comprises an A/D converter 6 converting the analog signals into digital signals.

Preferably, the A/D converter 6 is provided above or under the elongated plate of the substrate 4.

Preferably, the A/D converter 6 is provided under the substrate 4 and a shielding piece 5 is provided between the substrate 4 and the visible light to analog signal converter 3.

Preferably, the A/D converter 6 is provided under the substrate 4 and a shielding piece 5 is embedded into the upper end of the substrate 4.

In addition, CT apparatus further includes a heat sink 7 provided on the side of the A/D converter 6 which is away from the substrate 4.

The shielding piece 5 uses a high density material.

The thermal expansion coefficient of the shielding piece 5 is close to that of the visible light to analog signal converter 3.

Since the front-lit detector included in the CT apparatus is similar to the front-lit detector, it will not be described in detail any more.

While the specific embodiments of the present invention has been described above in conjunction with the drawings, various changes, modifications and equivalent substitutions can be made to the present invention by those skilled in the art without departing from the spirit and scope of the present invention. Thus such changes, modifications and equivalent substitutions are intended to fall within the spirit and scope of the appended claims.

The invention claimed is:

1. A front-lit detector comprising:
 a collimator;
 an X-ray to visible light converter configured to convert X-rays to visible light after the X-rays pass through the collimator to irradiate the X-ray to visible light converter;
 a visible light to analog signal converter configured to cover the visible light into analog signals;
 a substrate on which the visible light to analog signal converter is placed;
 a shielding piece embedded into an upper end of the substrate; and
 an A/D converter configured to convert the analog signals into digital signals.

2. The front-lit detector according to claim 1, wherein the A/D converter is provided above an elongated plate of the substrate.

3. The front-lit detector according to claim 1, wherein the A/D converter is provided under the substrate, where the shielding piece is provided between the substrate and the visible light to analog signal converter.

4. The front-lit detector according to claim 2, further comprising a heat sink provided on a side of the A/D converter that is away from the substrate.

5. The front-lit detector according to claim 3, wherein the shielding piece comprises a high density material.

6. The front-lit detector according to claim 5, wherein a thermal expansion coefficient of the shielding piece is close to a thermal expansion coefficient of the visible light to analog signal converter.

7. A method of placing an A/D converter in a front-lit detector, the front-lit detector including a collimator, an X-ray to visible light converter, a visible light to analog signal converter and a substrate, wherein X-rays irradiate on the X-ray to visible light converter after passing through the collimator, the X-ray to visible light converter configured to covert the X-rays into visible light, the visible light to analog signal converter placed on the substrate and configured to convert the visible light into analog signals, the method comprising:
 positioning the A/D converter at a position on the substrate that is not irradiated by the X-rays; and
 embedding a shielding piece into an upper end of the substrate.

8. The method according to claim 7, wherein positioning the A/D converter at a position on the substrate further comprises:
 elongating the substrate;
 positioning the A/D converter above the elongated plate of the substrate.

9. The method according to claim 7, wherein positioning the A/D converter at a position on the substrate further comprises:
 positioning the A/D converter under the substrate; and
 positioning the shielding piece between the substrate and the visible light to analog signal converter.

10. The method according to claim 8, further comprising providing a heat sink on a side of the A/D converter which is away from the substrate.

11. The method according to claim 9, further comprising providing a shielding piece including a high density material.

12. The method according to claim 11, wherein providing a shielding piece further includes providing a shielding piece having a thermal expansion coefficient that is close to a thermal expansion coefficient of the visible light to analog signal converter.

13. A CT apparatus comprising:
 a front-lit detector that comprises:
  a collimator;
  an X-ray to visible light converter configured to convert X-rays to visible light after the X-rays pass through the collimator to irradiate the X-ray to visible light converter;
  a visible light to analog signal converter configured to convert the visible light into analog signals;
  a substrate on which the visible light to analog signal converter is placed;
  a shielding piece embedded into an upper end of the substrate; and
 an A/D converter configured to convert the analog signals into digital signals.

14. The CT apparatus according to claim 13, wherein the A/D converter is provided above an elongated plate of the substrate.

15. The CT apparatus according to claim 13, wherein the A/D converter is provided under the substrate, where the shielding piece is provided between the substrate and the visible light to analog signal converter.

16. The CT apparatus according to claim 14, further comprising a heat sink provided on a side of the A/D converter that is away from the substrate.

17. The CT apparatus according to claim 15, wherein the shielding piece comprises a high density material.

* * * * *